United States Patent
Nolte et al.

(10) Patent No.: US 9,524,717 B2
(45) Date of Patent: Dec. 20, 2016

(54) SYSTEM, METHOD, AND COMPUTER PROGRAM FOR INTEGRATING VOICE-TO-TEXT CAPABILITY INTO CALL SYSTEMS

(71) Applicant: Trevo Solutions Group LLC, Lees Summit, MO (US)

(72) Inventors: Mark Nolte, Lees Summit, MO (US); Ryan Calder, Liberty, MO (US); Benjamin Loss, Kansas City, MO (US)

(73) Assignee: Trevo Solutions Group LLC, Lee's Summit, MO (US)

( * ) Notice: Subject to any disclaimer, the term of this patent is extended or adjusted under 35 U.S.C. 154(b) by 129 days.

(21) Appl. No.: 14/514,918

(22) Filed: Oct. 15, 2014

(65) Prior Publication Data

US 2015/0106092 A1 Apr. 16, 2015

Related U.S. Application Data

(60) Provisional application No. 61/891,157, filed on Oct. 15, 2013.

(51) Int. Cl.
| | | |
|---|---|---|
| G10L 15/26 | (2006.01) | |
| H04M 3/42 | (2006.01) | |
| H04M 3/51 | (2006.01) | |
| G06Q 50/24 | (2012.01) | |
| G06Q 50/22 | (2012.01) | |
| G10L 25/72 | (2013.01) | |

(Continued)

(52) U.S. Cl.
CPC .......... *G10L 15/26* (2013.01); *H04M 3/42221* (2013.01); *H04M 3/51* (2013.01); *G06Q 50/22* (2013.01); *G06Q 50/24* (2013.01); *G10L 15/30* (2013.01); *G10L 25/69* (2013.01); *G10L 25/72* (2013.01); *H04M 2201/40* (2013.01)

(58) Field of Classification Search
CPC .......... G10L 15/30; G10L 15/00; G10L 15/26; G10L 15/265; G10L 2015/221; G10L 15/222; G10L 15/223; G10L 15/225; G10L 25/69; G10L 25/72; G06Q 50/22; G06Q 50/24
See application file for complete search history.

(56) References Cited

U.S. PATENT DOCUMENTS 6,606,598 B1 * 8/2003 Holthouse ............... G10L 15/01
704/236
7,881,939 B2 * 2/2011 Tice ..................... H04L 12/2818
340/539.11

(Continued)

FOREIGN PATENT DOCUMENTS

| CH | EP 1385148 A1 * | 1/2004 | ............. G10L 15/22 |
| DE | EP 1067512 B1 * | 12/2007 | ............. G10L 15/18 |

OTHER PUBLICATIONS

EP 1385148 A1 and EP 1067512B1.*

*Primary Examiner* — Richard Zhu
(74) *Attorney, Agent, or Firm* — Hovey Williams LLP

(57) ABSTRACT

An interface for handling patient requests in voice calls sent from a call system includes a voice recognition engine that processes the voice calls and generates text data based on the requests, an analytics and reporting engine that improves efficiency of the voice recognition engine, and an alarm and routing engine that formats the text data for transmitting the text data to an intended recipient.

13 Claims, 4 Drawing Sheets

(51) Int. Cl.
*G10L 25/69* (2013.01)
*G10L 15/30* (2013.01)

(56) References Cited

U.S. PATENT DOCUMENTS

| | | | | |
|---|---|---|---|---|
| 8,183,987 B2 * | 5/2012 | Traughber | ............. | G06Q 50/22 340/286.02 |
| 8,315,245 B2 * | 11/2012 | Savoor | ............... | H04L 12/6418 370/229 |
| 8,416,930 B2 * | 4/2013 | Liang | ................. | H04M 3/5238 379/112.04 |
| 8,451,101 B2 * | 5/2013 | Somasundaram | ... | G08B 3/1033 340/286.07 |
| 8,583,439 B1 * | 11/2013 | Kondziela | .............. | G10L 15/22 379/189 |
| 8,635,066 B2 * | 1/2014 | Morrison | ........... | G06K 9/00221 704/231 |
| 8,954,325 B1 * | 2/2015 | Bokish | .................... | G10L 15/02 704/244 |
| 9,070,357 B1 * | 6/2015 | Kennedy | ................. | G10L 15/00 |
| 2002/0172335 A1 * | 11/2002 | Narasimhan | ........ | G06F 19/3418 379/106.02 |
| 2003/0120517 A1 * | 6/2003 | Eida | ....................... | G06Q 50/24 705/3 |
| 2006/0253281 A1 * | 11/2006 | Letzt | ...................... | G10L 15/30 704/231 |
| 2007/0005206 A1 * | 1/2007 | Zhang | ...................... | G06F 3/16 701/36 |
| 2007/0106685 A1 * | 5/2007 | Houh | ................. | G06F 17/30796 |
| 2009/0024411 A1 * | 1/2009 | Albro | .................... | G06F 19/322 705/2 |
| 2009/0132254 A1 * | 5/2009 | Fitzgerald | ........... | G06F 19/3487 704/270 |
| 2011/0022389 A1 * | 1/2011 | Kim | ....................... | G10L 15/07 704/246 |
| 2014/0122081 A1 * | 5/2014 | Kaszczuk | ............... | G10L 13/08 704/260 |

* cited by examiner

SYSTEM, METHOD, AND COMPUTER PROGRAM FOR INTEGRATING VOICE-TO-TEXT CAPABILITY INTO CALL SYSTEMS

RELATED APPLICATIONS

The present application is a non-provisional application and claims priority benefit, with regard to all common subject matter, of earlier-filed U.S. provisional patent application titled "SYSTEM, METHOD, AND COMPUTER PROGRAM FOR INTEGRATING VOICE-TO-TEXT CAPABILITY INTO CALL SYSTEMS," Ser. No. 61/891,157, filed Oct. 15, 2013. The identified earlier-filed application is hereby incorporated by reference in its entirety into the present application.

BACKGROUND

Many hospital patient rooms are connected to nurse call systems via patient call devices to allow patients to communicate with the clinical staff of the hospital. Many such nurse call systems have been automated and centralized for handling increasing numbers of patients. Nurse call system manufacturers have also added more buttons to the patient call devices for handling more diversified patient requests.

Existing nurse call systems have many inefficiencies and result in many reports of patient dissatisfaction and even cases of compromised patient safety. For example, in centralized nurse call systems, the chance of a nurse or operator being unable to answer a patient call is increased. The unattended audio alerts from unanswered patient calls create a noisy and unrestful environment. On the other hand, in decentralized nurse call systems, calls to nurses often interrupt patient care. The costs of implementing infrastructure and staffing to support existing nurse call systems are also substantial. These same issues are found in communication systems used in other applications.

SUMMARY

The present invention solves the above-described problems and provides a distinct advance in the art of call systems. More particularly, the present invention provides an interface that converts spoken requests from a call system into text data and analyzes the text data to improve future request-to-text conversions. The text data may be any kind of discrete text information such as the text of a text message or word processor file.

Aspects of the present invention may be at least partially implemented with a nurse call system that allows patients of one or more hospitals or caregiving facilities to make patient requests such as asking for bathroom assistance or indicating a worsening health condition. The nurse call system may include a number of patient call devices located in the hospital rooms, a wired or wireless network for transmitting the patient requests, and optionally a patient request receiving computer. The present invention may also be used with call systems for restaurants, hotels, transportation companies, and other service industries, and police, fire, medic, and other emergency services. For example, aspects of the present invention may be at least partially implemented with a taxi call system that allows potential riders to request a taxi.

An interface constructed in accordance with an embodiment of the present invention broadly includes a telephony engine, a voice recognition engine, an alarm and routing engine, an analytics and reporting engine, and a mobile engine. The telephony engine answers and manages patient voice calls. The voice recognition engine processes the voice call and converts the voice messages to text data. The alarm and routing engine manipulates converted text data and interfaces with an alert management system (AMS). The analytics and reporting engine monitors and reports on the efficiency and accuracy of the voice recognition engine. The mobile engine provides access to administrators for troubleshooting and modifying operating parameters of the nurse call system via a mobile application installed on an administrator's mobile device.

The AMS receives the text data in text message form or converts the text data into a text message and routes the text message to the mobile device of a nurse, caregiver, or other intended recipient.

The mobile devices allow the nurses or other recipients to receive text messages and/or alerts based on the text, acknowledge receipt of the patient requests, and respond to the patient requests accordingly. The mobile devices may be cell phones, tablets, laptops, or other similar computing devices.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

Figure 1:
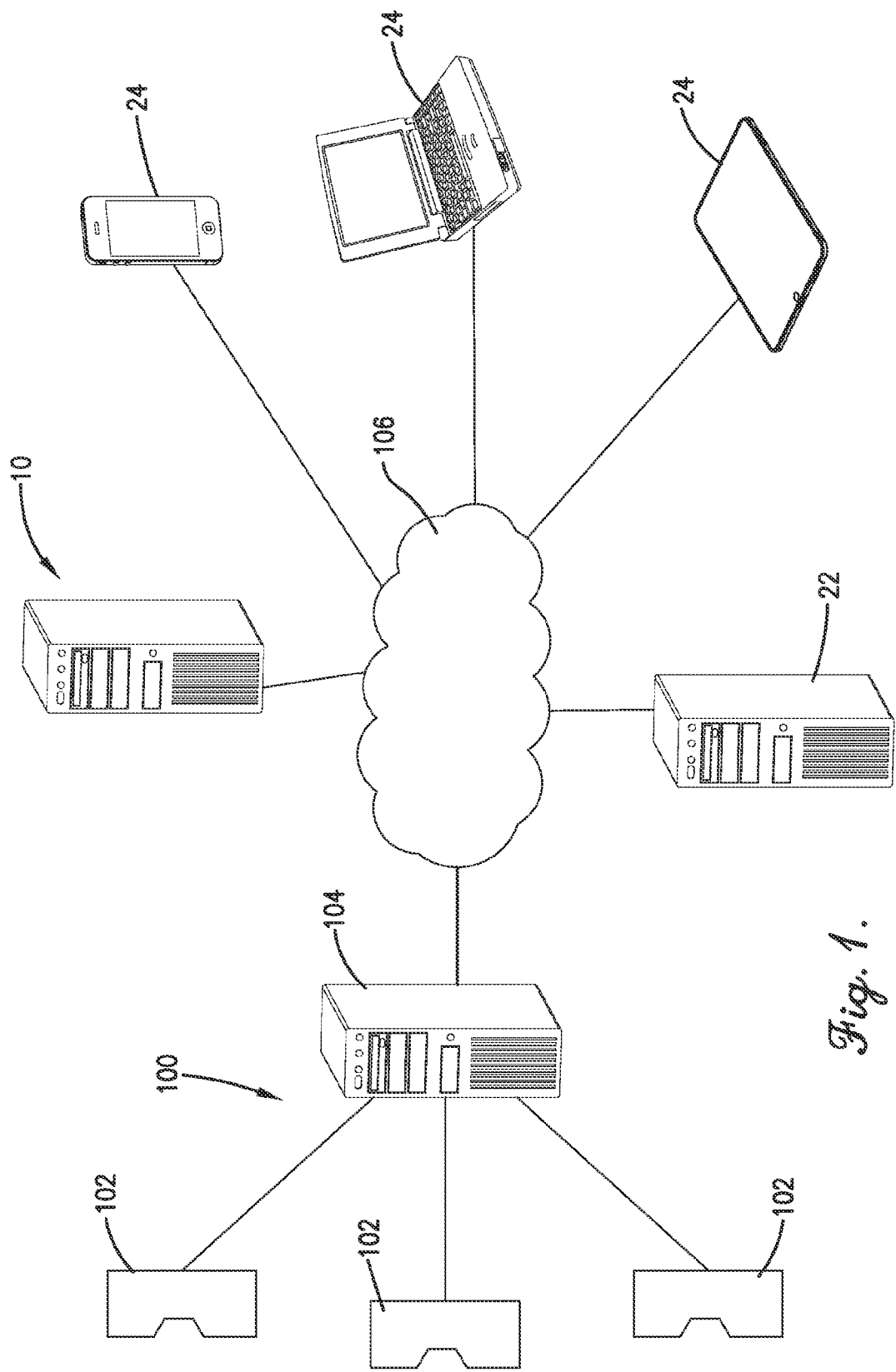
FIG. 1 is a schematic view of a call system, an interface constructed in accordance with an embodiment of the invention, and a number of mobile devices.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Aspects of the present invention may be at least partially implemented with or coupled with a call system such as a nurse call system for managing patient requests (e.g., "nurse calls") broadly referred to by the numeral 100 in FIG. 1. The present invention may also be used with call systems for restaurants, hotels, transportation, and other service industries, and police, fire, medic, and other emergency services.

The nurse call system 100 allows patients of one or more hospitals or caregiving facilities to make patient requests such as asking for bathroom assistance or indicating a worsening health condition. The nurse call system 100 may include a number of patient call devices 102 located in the hospital rooms near or on each patient's bed, a wired or wireless network for transmitting the patient requests, and optionally a patient request receiving computer 104.

The patient call devices 102 allow patients to make voice calls for nurse assistance and other aid and may include an interface having buttons, dials, and other inputs and a microphone, a speaker, and a display screen. The patient call devices 102 may be wired to the network or may include a transceiver for wirelessly transmitting and receiving voice data over the network.

The network connects the patient call devices 102 to the patient request receiving computer 104 and may be any communication network such as a local area network, wide area network, an intranet, the Internet, any radio frequency network, or any other wired or wireless network capable of supporting communications such as the wireless networks operated by AT&T, Verizon, or Sprint.

The patient request receiving computer 104 receives the patient voice requests from the patient call devices 102 and routes them via a network 106 (described below) or similar connection using session initiation protocol (SIP) or similar protocol. The patient request receiving computer 104 may include one or more computers, similar to the computers described below, for performing the routing function.

The network 106 may be any communication network such as a local area network, wide area network, an intranet, the Internet, any radio frequency network, or any other wired or wireless network capable of supporting communications such as the wireless networks operated by AT&T, Verizon, or Sprint. The network 106 may be the same network as the network connecting the patient call devices 102 and the patient request receiving computer 104.

Figure 2:
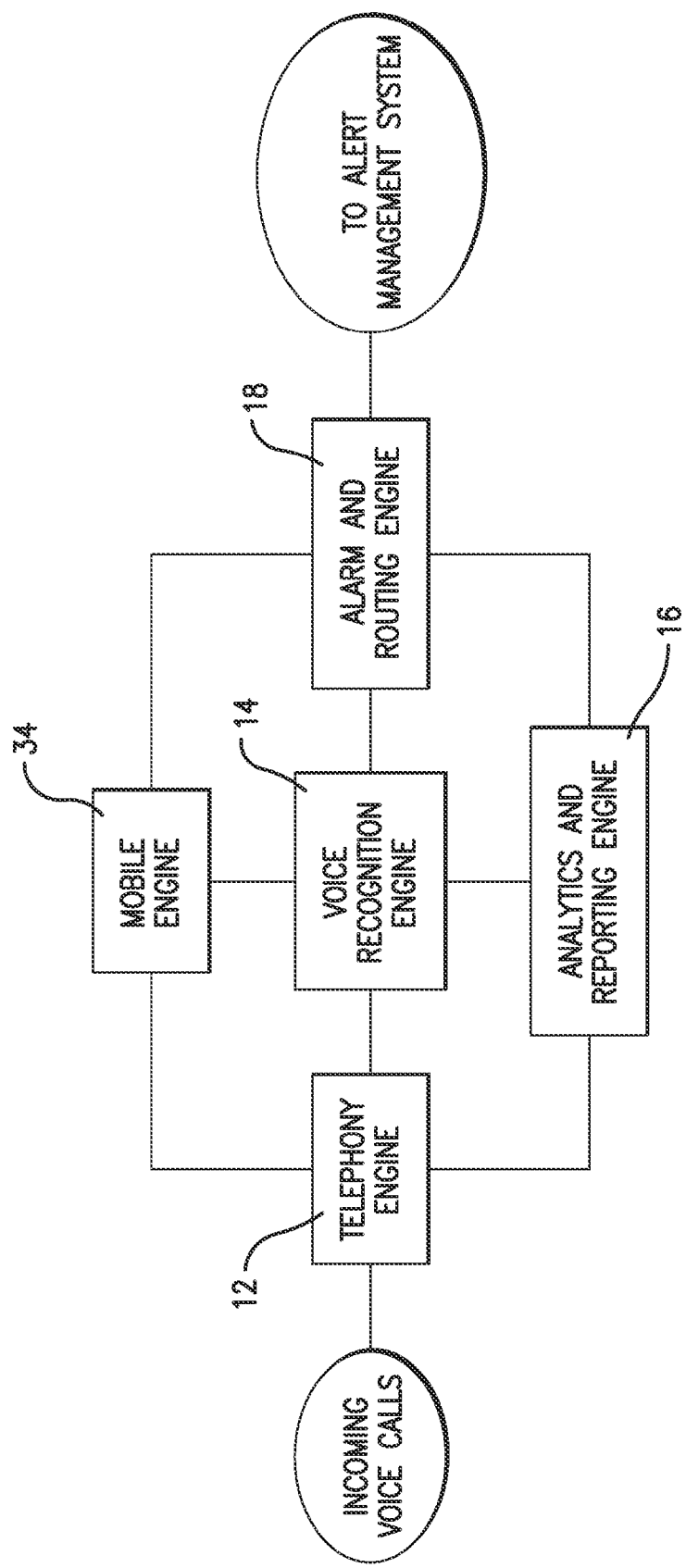
FIG. 2 is a block diagram of components of the interface of FIG. 1.

An interface 10 constructed in accordance with one embodiment of the invention broadly includes one or more computers running a telephony engine 12, a voice recognition engine 14, an analytics and reporting engine 16, an alarm and routing engine 18, and a mobile engine 20, as shown in FIG. 2.

The interface 10 may be separate from the nurse call system 100 or other messaging or alarm management system and may include a computing device such as a network computer running Windows, Novel Netware, Linux, Unix, iOS, OS X, Android, or any other operating system. In some embodiments, the interface 10 includes a computing device that has its own processor and memory and is housed in a separate housing. The interface 10 may be connected to another computing device operated by an administrator of the interface 10 via another communication network. Alternatively, the interface 10 may be a plurality of component devices such as peripheral component interconnect (PCI) cards or personal computer memory card international association (PCMCIA) cards that can be placed into a host computing device. The processor may include microprocessors, microcontrollers, programmable intelligent computers (PICs) and the like. The processor may also include field-programmable gate arrays (FPGAs), other programmable logic devices (PLDs), fully-custom or semi-custom application-specific integrated circuits (ASICs), or any other device that is described by one or more code segments of a hardware description language (HDL). The memory generally stores interface licensing information, interface settings, and a database of call locations, call strings, client identifications, and other information for the operation of the interface 10 in the form of a database, spreadsheet, text file, binary code, XML file, RSS feed, raw data, or other form of computer-readable data. The data may be initially hidden, encrypted, or otherwise secure, un-editable, disabled, or inconveniently or indirectly accessible. The data may be revealed, decrypted, made editable, enabled, more easily or directly accessed, purchased, downloaded, or changed by other components of the interface 10. The memory may include, for example, removable and non-removable memory elements such as random-access memory (RAM), read-only memory (ROM), flash, solid state, magnetic, optical, USB memory devices, and/or other conventional memory elements such as hard-disk drives. The interface 10 may also include a computer display and/or user interface for allowing a user or administrator to input commands into the interface 10 and a transceiver or an interface such as a universal serial bus (USB), Ethernet port, telephone port, VoIP device, asterisk box, telephone switch, or proprietary interface for communicating with other computing devices including an alert management system 22 (described below) and accepting calls from the patient call devices 102 via the network 106.

The display allows a user or administrator to view interface outputs and may include a graphical interface for displaying visual graphics, images, text, and other information in response to external or internal processes and commands. For example, the display may comprise conventional black and white, monochrome, or color display elements including CRT, TFT, LCD, and/or LED display devices. The display may be integrated with a user interface (described below) wherein the display is a touch screen display for enabling the user to interact with it by touching or pointing at display areas to provide information to the interface 10. The display may be coupled with various other components of the interface 10 and may be operable to display various information corresponding to the nurse call system 100, the telephony engine 12, the voice recognition engine 14, the alarm and routing engine 18, the analytics and reporting engine 16, the mobile engine 20, and/or the alert management system 22.

The user interface enables one or more users to share information and commands with the interface 10 such as information about the nurse call system 100, information about the alert management system 22, and configuration settings of the telephony engine 12, voice recognition engine 14, analytics and reporting engine 16, the alarm and routing engine 18, and mobile engine 20. The user interface may comprise one or more inputs such as buttons, switches, scroll wheels, a touch screen, a microphone, a pointing device such as a mouse, touchpad, tracking ball, or stylus, a camera or video camera, an optical scanner, or combinations thereof. The user interface may also include a speaker for providing audible instructions and feedback and wired or wireless data transfer elements such as a removable memory and a transceiver for enabling the user and other devices or parties to remotely communicate with the interface 10. The user interface may include a virtual dashboard for displaying previous calls, voice-to-text success data, current state of a call, success of a current voice-to-text conversion, and call locations and for playing a message recording, as described below.

The interface 10 further includes a computer program stored on computer-readable medium residing on or accessible by the interface 10 for instructing the interface 10 to operate certain steps of the present invention as described herein. Portions of the computer program stored on memories of the interface 10 can be updated via a computer readable medium, the network 106, or a manual connection. Therefore, the computer program as described herein is to be understood as all code segments, either individually or collectively, that are executed to implement the steps and features of the present invention.

The computer program can be embodied in any computer-readable medium for use by or in connection with an instruction execution system, apparatus, or device, such as a computer-based system, processor-containing system, or other system that can fetch the instructions from the instruction execution system, apparatus, or device, and execute the instructions. In the context of this application, a "computer-readable medium" can be any means that can contain, store, communicate, propagate or transport the program for use by or in connection with the instruction execution system, apparatus, or device. The computer-readable medium can be, for example, but not limited to, an electronic, magnetic, optical, electro-magnetic, infrared, or semi-conductor system, apparatus, device, or propagation medium. More specific, although not inclusive, examples of the computer-readable medium include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM). The computer-readable medium could even be paper or another suitable medium upon which the program is printed, as the program can be electronically captured, via optical scanning of the paper or other medium, then compiled, interpreted, or otherwise processed in a suitable manner, if necessary, and then stored in a computer memory. The various actions and calculations described herein as being performed by or using the computer program may actually be performed independently or cooperatively by one or more computers, processors, or other computational devices.

The telephony engine 12 answers and manages voice calls and may include an audible prompt when answering calls to indicate that the interface 10 is ready to capture an audible request. The telephony engine may set a maximum number of concurrent calls that the interface 10 can answer. For example, if a license allows for five concurrent calls, any calls exceeding this limit would roll over to a central call center or a predetermined call center. In another embodiment, the telephony engine 12 may be configured to answer all incoming calls. Alternatively, the telephony engine 12 may be configured to only answer calls that are not answered after a predefined number of rings. The maximum number of concurrent calls allowed by the interface 10 would also be dependent on the hardware capable of supporting the number of calls (known as "asterisk boxes" or "telephone switches"). The telephony engine 12 (or the nurse call system 100) may support direct routing of voice calls to a human who may transcribe pertinent information when the voice calls are coming from speakers for whom poor quality speech (e.g., low volume, mumbled or slurred words) is expected.

The voice recognition engine 14 processes the voice calls and may immediately process a live voice call or may process a recording of a voice call. Some or all of the voice calls may be recorded for future playback. The voice recognition engine 14 may also be programmed for recording retention periods or criteria for recorded voice calls. The voice recognition engine 14 generates text data based on the words and phrases of the patient request. The voice recognition engine 14 may transcribe the voice calls into text with less than 100 percent accuracy. For this reason the voice recognition engine 14 may record the audio of the voice calls for review by intended recipients. The recordings may be accessed as described below. The voice recognition engine 14 assigns a confidence score to snippets of recognized speech from the voice calls. The confidence score indicates how confident the voice recognition engine 14 is that it has correctly recognized the speech in the voice calls. Factors that may reduce a confidence score may include high levels of background noise, messages spoken in a low volume, messages spoken with mumbled or slurred words, messages spoken in a language other than the expected language, more than one person speaking at once, and the caller talking away from the microphone of the patient call device 102.

The voice recognition engine 14 improves its voice recognition over time. The voice recognition engine 14 may perform an algorithm that begins with a base vocabulary and increases the vocabulary based on words commonly used at a given hospital or site. The algorithm may also focus on a vocabulary of commonly used words that identify requests common to the industry, wherein the focus on the smaller vocabulary increases the success rate of accurate conversion of voice to text. For example, in the health care industry, the voice recognition engine 14 may focus on a preliminary or configurable vocabulary of commonly used words identified in patient requests such as "bathroom", "pills", "medicine", "cold", and "hurt". Alternatively, if used in the hotel industry, the voice recognition engine 14 would focus on words such as "luggage", "room service", and "valet". The voice recognition engine 14 may flag messages that it is unable to process for the delivery of the entire recorded message to an intended recipient.

The analytics and reporting engine 16 monitors and reports on the efficiency and accuracy of the interface 10 and may analyze and/or compile data on the success rate of voice recognition of the interface 10, frequently missed phrases, calls by type (e.g., pain, drink, bathroom assistance), or any other statistic associated with the performance of the interface 10. The analytics and reporting engine 16 may also create a report or other human-readable output documenting its analysis. The reports may include additional data about the voice calls and statistics on interface performance. For example, the report could include a list of the most common key words used or the frequency of requests by patient or department.

The alarm and routing engine 18 allows the interface 10 to communicate with the alert management system 22. In one embodiment, the alarm and routing engine 18 formats the text messages received from the interface 10 into a format expected by the alert management system 22 via a call string. Alternatively, the alarm and routing engine 18 will package the formatted message into a discrete data element that is compatible with the alert management system 22. The alarm and routing engine 18 may incorporate a mapping of nurse call locations, call strings, request type, and client identifications to ensure that the alert management system 22 can properly route the messages, as described in more detail below. The alarm and routing engine 18 may transmit a message including metadata but not transmit the text data transcription if the text data transcription has a confidence score below a predetermined threshold. The alarm and routing engine 18 (or the voice recognition engine 14) may flag calls with low confidence scores for additional attention from staff members. The alarm and routing engine 18 may also control whether the interface 10 will handle calls in a primary or secondary mode in the event of a predetermined condition set by an administrator or in the event of a failed voice-to-text conversion. In the primary mode, the interface 10 may deliver messages to an intended recipient either as a text message or as the entire original voice message as recorded. In the secondary mode, the interface 10 may route calls to a predetermined call center either for live conversation with a representative or other actual person or for the manual translation of voice to text by an actual person. The predetermined call center can be a national call center, a regional call center, a hospital call center, or a unit level call center where a human interaction between the caller and an operator may take place. In such a case, the operator may transcribe the caller's request into a text message that is sent to the interface 10 and routed to the intended recipient via the alert management system 22. In one embodiment, the call center is a nationwide call center for processing calls from locations across the United States or any other country. In a healthcare setting, this could free hospitals from having to staff a nurse station twenty-four hours per day while providing 100% coverage of patient calls with the benefit of human interaction and relieving caregivers from spending time answering patient calls.

The alarm and routing engine 18 may also route calls to an appropriate destination based on a predefined set of rules as set by the administrator. In the healthcare setting, rules may be based on a range of room numbers, patients' primary languages, unit types, patients' age groups, patient ailments, or other data typically sent from the originating patient call devices 102. These calls can be handled by the interface 10 for voice-to-text interfacing to the alert management system 22, routed to the predefined call center as defined herein, or sent to the intended recipient as an untranslated "voicemail-type" message recording or saved and linked via a call-back URL for the recipient to play at a later time. In these cases, the message is stored on a server for a predetermined period of time or indefinitely. The interface 10 may also store voice or text files on local memory or on a remote server before communicating a link to the voice or text data and to the alert management system 22 for routing and delivery.

The mobile engine 20 provides access to administrators for troubleshooting and modifying operating parameters of the nurse call system via a mobile application installed on a mobile device. The mobile engine 20 may provide system statistics to administrators and may allow administrators to modify the interface 10 or parameters of the interface 10. The mobile application may include a virtual interface that allows administrators to easily make these modifications.

The mobile device allows an administrator to run the mobile engine 20 and may be a smartwatch, smartphone, tablet, laptop, or any other portable computing device. The mobile device may be one of the mobile devices 24 described below.

The alert management system (AMS) 22 receives the text data in text message form from the interface 10 or converts the text data into a text message and routes the text message to the appropriate nurse mobile device 24 or other nurse computing device.

The mobile devices 24 allow the nurses to receive patient request text messages, alerts, or notifications and each device may be a pager, smartwatch, smartphone, tablet, laptop, personal digital assistant (PDA), or any other portable computing device. The mobile devices 24 each include a memory, a processor, a transceiver, and a display as described above.

Figure 3:
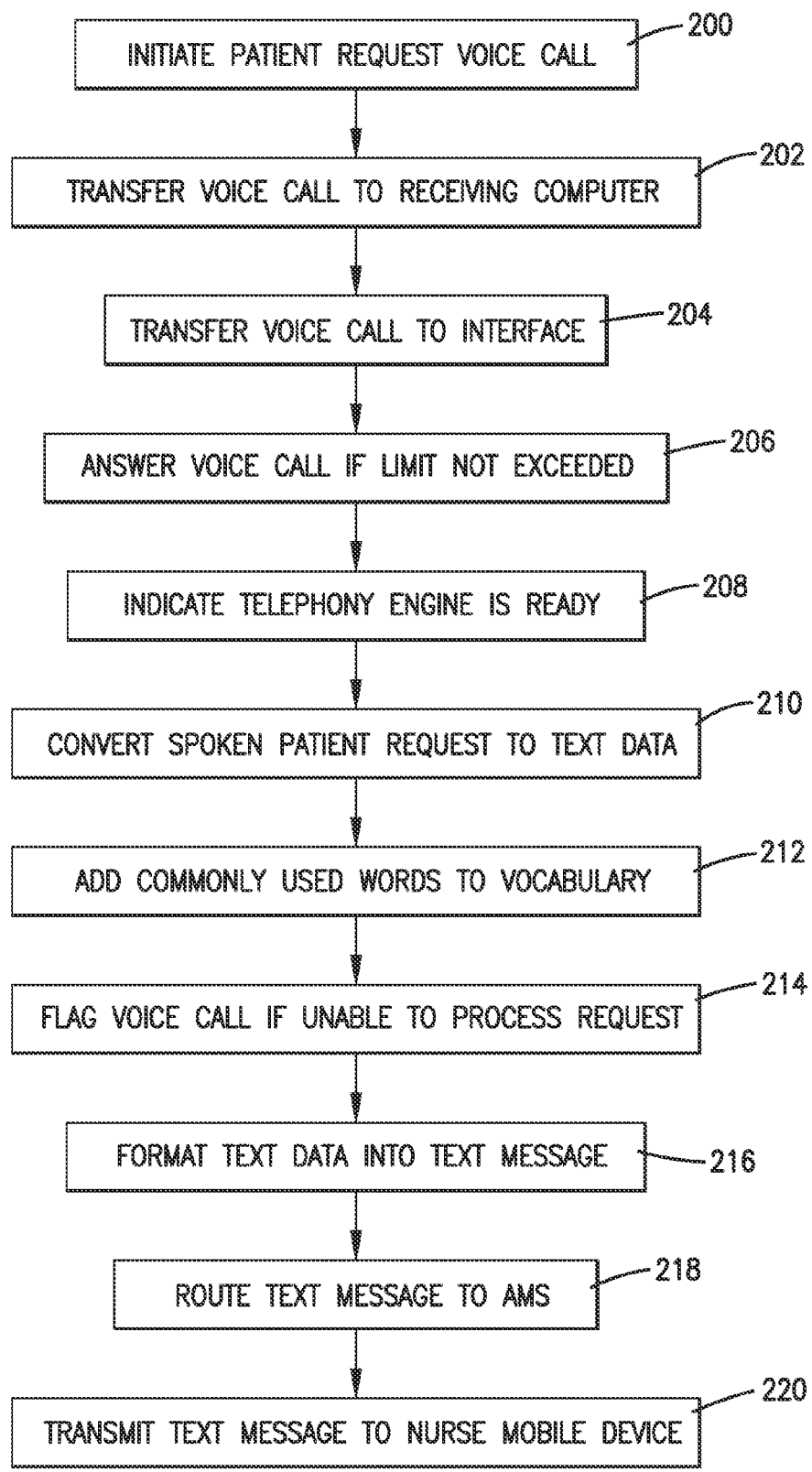
FIG. 3 is a flow chart of a method of integrating voice-to-text message conversion between requests (e.g., "nurse calls")

Use of the interface 10 will now be described with reference to the flow chart of FIGS. 3 and 4. A patient staying at a hospital or other caregiving facility may first initiate a patient request in the form of an audio voice call on one of the patient call devices 102, as shown in block 200.

The patient call device 102 transmits the voice call wirelessly via the network or through a wired infrastructure to the patient request receiving computer 104, as shown in block 202.

The patient request receiving computer 104 then transmits the voice call via the network 106 to the interface 10, as shown in block 204. Alternatively, the patient call device 102 may transmit the voice call directly to the interface 10.

The telephony engine 12 of the interface 10 answers the voice call transmitted form the patient call device 102 if the voice call causes the number of answered calls to exceed a concurrent call limit, as shown in block 206. If the concurrent call limit is exceeded, the telephony engine 12 may redirect the voice call to a central call center or a predetermined call center. The telephony engine 12 may also answer the voice call if the voice call causes the number of answered calls to exceed a license limit or volume limit over a defined period. For example, the telephony engine 12 could be limited to answering 500 calls per day. Alternatively or in addition, a cost-per-voice call could be implemented.

The telephony engine 12 may deliver an audible prompt to the patient call device 102 to indicate that the telephony engine 12 is ready to capture the patient request, as shown in block 208.

The voice recognition engine 14 then converts the spoken words or phrases of the patient request into text messages or text data, as shown in block 210.

The voice recognition engine 14 adds commonly used words from the patient request to its vocabulary for improving voice-to-text conversion accuracy and efficiency, as shown in block 212.

The voice recognition engine 14 flags the voice call if it is unable to process the entire patient request, as shown in block 214.

The alarm and routing engine 18 then formats the text message or text data from the interface 10 into an AMS compatible format via a call string or the alarm and routing engine 28 formats the text message or text data into an AMS compatible discrete data element and includes AMS routing information and/or other metadata, as shown in block 216.

The alarm and routing engine 18 then routes the text message or text data to the AMS 22, as shown in block 218.

The AMS 22 then transmits the text message or text data or transmits a notification such as an alert representative of the contents of the text message or text data to the appropriate nurse, caregiver, doctor, unit clerk, or other hospital staff member, as shown in block 220.

Figure 4:
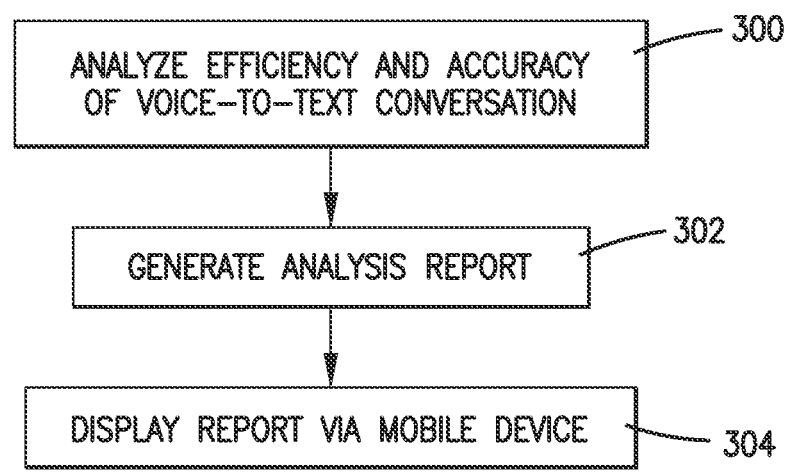
FIG. 4 is a flow chart of steps for analyzing and reporting efficiency and accuracy of the voice recognition engine of FIG. 2.

The interface 10 improves the efficiency and accuracy of the voice-to-text conversion, as shown in FIG. 4. The analytics and reporting engine 16 analyzes the current efficiency and accuracy of the voice-to-text conversion and compiles data such as success rate, frequently missed phrases or words, most commonly missed phrases or words, calls by type, number of calls by patient or department and other statistics, as shown in block 300.

The analytics and reporting engine 16 then generates a report of its analysis such as a graph or table for administrative review, as shown in block 302.

The report is then presented on a display of an administrator's mobile device such as a smartphone, tablet, or laptop, or delivered electronically via email or similar communication method, as shown in block 304.

Some of the blocks of the flow chart may represent a step or steps in a method or a module segment or portion of the computer programs of the present invention. In some alternative implementations, the functions noted in the various blocks may occur out of the order depicted in FIGS. 3 and 4. For example, two blocks shown in succession in FIG. 3 may in fact be executed substantially concurrently, or the blocks may sometimes be executed in the reverse order depending upon the functionality involved.

Embodiments of the present invention provide significantly more than the application of an abstract idea using a generic computer and provide advancements to the field of call systems and managing requests. For example, the interface 10 converts the patient requests to text and analyzes the text to improve patient request response accuracy, efficacy, and efficiency. The interface 10 delivers more accurate information to the nurses, delivers more useful information and more quickly delivers the information, delivers information that allows nurses to more quickly respond to the patient requests after receiving the information, and adapts to changes or trends in patient requests and caregiving techniques and guidelines. Prior art approaches have not incorporated these features and simply deliver patient requests to nurses or nurse call centers without using information in the patient requests to improve the nurse call system.

The computer devices described herein are necessary to perform the calculations needed to convert voice messages to text and to analyze the text information. The conversion and analysis would require too much time for a human to perform, especially when a large number of patient requests are involved.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An interface for a call system, the interface comprising:
   a telephony engine configured to:
      receive a voice call from the call system, the voice call including a spoken request;
      automatically answer the voice call:
         if answering the voice call would not increase the number of concurrently answered voice calls to more than a pre-determined maximum number of concurrently answered voice calls, and
         only if the voice call is not answered after a pre-determined number of rings;
      transfer the voice call to a pre-determined call center if answering the voice call would increase the maximum number of concurrently answered voice calls to more than the pre-determined maximum number of concurrently answered voice calls;
   a voice recognition engine coupled with the telephony engine for analyzing the voice call and generating text data representative of at least a portion of the request, the call system being configured to:
      transmit the text data to a mobile device of a nurse or caregiver for responding to the patient request if converting the at least a portion of the patient request into text data is successful, and
      transmit the patient request to the mobile device of the nurse or caregiver in the form of a recording of the voice call if converting the at least a portion of the patient request into text data is unsuccessful; and
   an analytics and reporting engine configured to analyze a success rate of voice-to-text conversion performed by the voice recognition engine and report results of the analysis.

2. The interface of claim 1, further comprising an alarm and routing engine for formatting the text data and for directing the text data to an alert management system configured to route the text data to a mobile device or call center for responding to the request, wherein the alarm and routing engine is configured to determine whether a recording of the voice call will be routed to an intended recipient or the voice call will be routed to a predetermined call center for interpreting the request if the voice recognition engine is unable to generate text data representative of at least a portion of the request.

3. The interface of claim 1, further comprising a virtual dashboard for displaying previous calls, voice-to-text success data, current state of a call, success of a current voice-to-text conversion, and call locations and for playing a message recording.

4. The interface of claim 1, wherein the call center is a nationwide call center for processing calls from locations and/or organizations across the country.

5. The interface of claim 1, wherein the voice recognition engine is further configured to flag the voice call to be routed to a pre-determined call center for initiating a live conversation between a person initiating the request and a representative at the call center if the voice recognition engine is unsuccessful in converting the at least a portion of the request into text data.

6. The interface of claim 1, wherein the alarm and routing engine is configured to flag the voice call to be routed to one of a number of pre-determined call centers based on a pre-defined set of rules as set by an administrator.

7. The interface of claim 1, wherein the analytics and reporting engine is configured to flag unrecognizable words that the voice recognition engine has failed to convert to text.

8. The interface of claim 1, wherein the voice recognition engine includes a vocabulary and adds words commonly used in requests to the vocabulary from each request that is converted to text for improving request-to-text conversion accuracy and efficiency.

9. The interface of claim 1, wherein the telephony engine is configured to transmit an audible prompt to a call device of the call system upon answering the voice call to indicate that the telephony engine is ready to receive the request.

10. The interface of claim 1, wherein the voice recognition engine is configured to assign a confidence score to text data generated from recognized speech from the voice call, the confidence score being reduced by the following factors:
   a) background noise;
   b) low volume speech;
   c) mumbled or slurred speech;
   d) speech in a language other than an expected language;
   e) more than one person speaking at once; and
   f) a caller speaking away from a microphone of a call device.

11. The interface of claim 10, wherein the interface generates a recording of the voice call for review by an intended recipient and links to the recording for access by an intended recipient.

12. The interface of claim 11, wherein the interface appends metadata to the recording but does not append the text data to the recording if the confidence score is below a predetermined threshold.

13. A method for handling patient requests, the method comprising the steps of:
   transmitting a voice call containing a spoken patient request from a patient call device of a nurse call system to a patient request computer;
   transmitting the voice call from the patient request computer to a voice-to-text recognition interface having one or more computers including a non-transitory computer readable medium for storing a telephony engine and a voice recognition engine;
   automatically answering the voice call via the telephony engine if answering the voice call would not increase the number of concurrently answered voice calls to more than a pre-determined maximum number of concurrently answered voice calls;
   automatically answering the voice call only if the voice call is not answered after a pre-determined number of rings;
   transferring the voice call to a pre-determined call center if answering the voice call would increase the maximum number of concurrently answered voice calls to more than the pre-determined maximum number of concurrently answered voice calls;
   generating text data representative of at least a portion of the patient request via the voice recognition engine;
   transmitting the text data to a mobile device of a nurse or caregiver for responding to the patient request if converting the at least a portion of the patient request into text data is successful;
   transmitting the patient request to the mobile device of the nurse or caregiver in the form of a recording of the voice call if converting the at least a portion of the patient request into text data is unsuccessful;
   analyzing a success rate of voice-to-text conversion performed by the voice recognition engine;
   generating an analysis report of the success rate analysis; and
   displaying the analysis report on a graphical display.

* * * * *